(12) United States Patent
Shan et al.

(10) Patent No.: US 6,814,950 B1
(45) Date of Patent: Nov. 9, 2004

(54) INORGANIC OXIDES WITH MESOPOROSITY OR COMBINED MESO- AND MICROPOROSITY AND PROCESS FOR THE PREPARATION THEREOF

(75) Inventors: Zhiping Shan, Delft (NL); Thomas Maschmeyer, Delft (NL); Jacobus Cornelis Jansen, Delft (NL)

(73) Assignees: ABB Lummus Global Inc., Bloomfield, NJ (US); Technische Universiteit Delft, Delft (NL)

( * ) Notice: Subject to any disclaimer, the term of this patent is extended or adjusted under 35 U.S.C. 154(b) by 0 days.

(21) Appl. No.: 10/070,711

(22) PCT Filed: Mar. 16, 2000

(86) PCT No.: PCT/US00/07094

§ 371 (c)(1),
(2), (4) Date: Jul. 17, 2002

(87) PCT Pub. No.: WO01/17901

PCT Pub. Date: Mar. 15, 2001

Related U.S. Application Data

(63) Continuation-in-part of application No. 09/390,276, filed on Sep. 7, 1999, now Pat. No. 6,358,486.

(51) Int. Cl.[7] .......................... C01B 33/12; C01F 7/02
(52) U.S. Cl. ...................................... 423/326; 625/628
(58) Field of Search ............................. 423/326, 327.1, 423/327.2, 328.1, 328.2, 328.3, 329.1, 332, 625, 628, 701–707, 718, 334–339; 502/60, 62, 63, 64

(56) References Cited

U.S. PATENT DOCUMENTS

| | | | |
|---|---|---|---|
| 3,959,174 A | 5/1976 | Winyall et al. | 252/317 |
| 5,057,296 A | 10/1991 | Beck | 423/277 |
| 5,098,684 A | 3/1992 | Kresge et al. | 423/277 |
| 5,102,643 A | 4/1992 | Kresge et al. | 423/328 |
| 5,538,710 A | 7/1996 | Guo et al. | 423/701 |
| 5,601,798 A * | 2/1997 | Cooper et al. | 423/700 |
| 5,622,684 A | 4/1997 | Pinnavia et al. | 423/702 |
| 5,672,556 A | 9/1997 | Pinnavia et al. | 502/63 |
| 5,795,555 A | 8/1998 | Alive et al. | 423/326 |
| 5,811,612 A * | 9/1998 | Girotti et al. | 585/467 |
| 5,840,271 A * | 11/1998 | Carrazza et al. | 423/700 |
| 5,849,258 A | 12/1998 | Lujano et al. | 423/700 |
| 5,919,430 A | 7/1999 | Hasenzahl et al. | 423/702 |
| 6,358,486 B1 * | 3/2002 | Shan et al. | 423/326 |

FOREIGN PATENT DOCUMENTS

WO    WO00/15551    3/2000

OTHER PUBLICATIONS

Attard, et al., *Nature*, vol. 378, pp. 366–368 (Nov. 23, 1995).

* cited by examiner

*Primary Examiner*—Stanley S. Silverman
*Assistant Examiner*—Maribel Medina
(74) *Attorney, Agent, or Firm*—Elliot M. Olstein; Raymond J. Lillie

(57) ABSTRACT

Bimodal inorganic material that in a pore size distribution plot has distinct mesopore and micropore peaks. A process for producing a bimodal material or a material that contains essentially only mesopores involves heating an inorganic oxide in the presence of material that bonds to the inorganic oxide by hydrogen bonding. The micropores may or may not include a crystalline structure.

26 Claims, 15 Drawing Sheets

Example 1

Example 1

Example 2

Figure 1B: BJH Desorption dV/dlogD curve for the sample prepared according to example 1.

```
           Started: 03/29/99 08:55:09
         Completed: 03/30/99 18:09:56
       Report Time: 03/31/99 08:37:39
     Sample Weight: 0.1270 g
    Warm Freespace: 18.5791 cm³
    Equil. Interval: 10 secs
Analysis Adsorptive: N2
      Analysis Bath: 77.30 K
 Thermal Correction: No
  Smoothed Pressures: No
       Cold Freespace: 57.1148 cm³
     Low Pressure Dose: 5.00 cm³ /g STP
```

FIG. 1C

Figure 1C: Horvath-Kawazoe differential pore volume plot with slit pore geometry for the sample prepared according to example 1.

```
         Started: 03/29/99 08:55:09
       Completed: 03/30/99 18:09:56
     Report Time: 07/14/99 09:15:22
   Sample Weight: 0.1270 g
  Warm Freespace: 18.5791 cm³
 Equil. Interval: 10 secs
Analysis Adsorptive: N2
   Analysis Bath: 77.30 K
Thermal Correction: No
Smoothed Pressures: No
  Cold Freespace: 57.1148 cm³
Low Pressure Dose: 5.00 cm³ /g STP
```

Horvath-Kawazoe Differential Pore Volume Plot
Slit Pore Geometry (original HK)

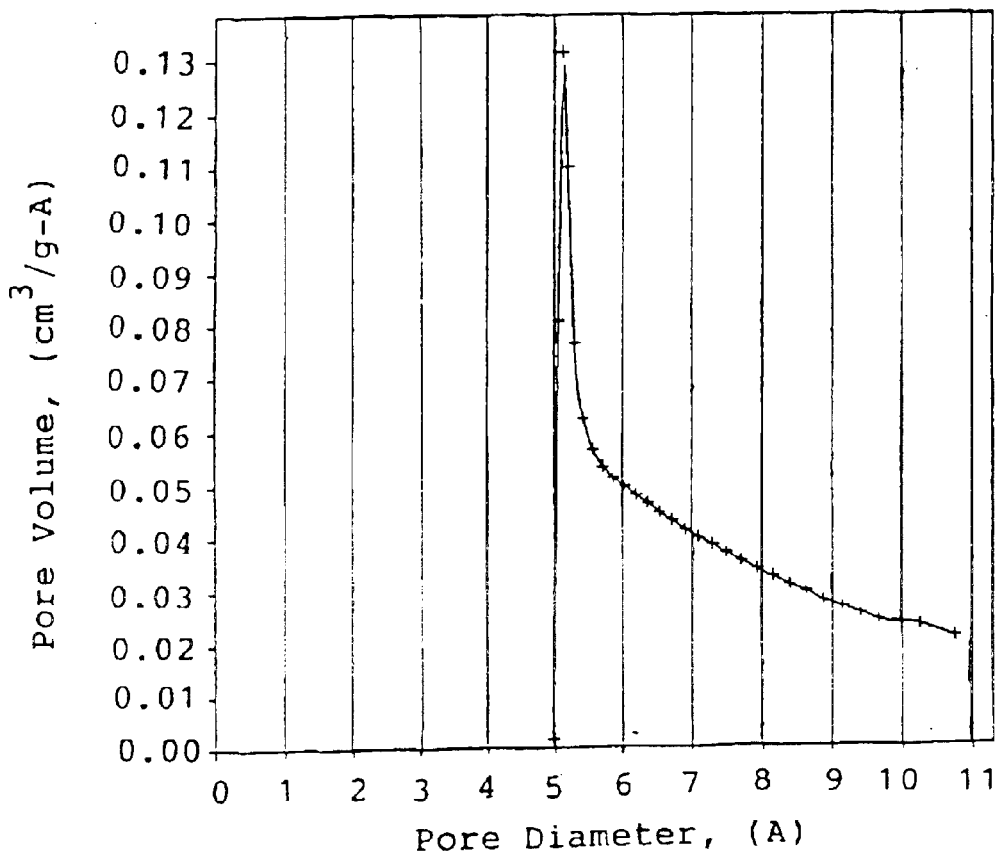

Figure 2 B: BJH Desorption dV/dlogD curve for the sample prepared according to example 2.

```
        Started:  03/18/99 11:49:36
      Completed:  03/20/99 02:27:11
    Report Time:  03/23/99 08:50:51
  Sample Weight:  0.3600 g
  Warm Freespace: 17.3334 cm³
  Equil. Interval: 10 secs
Analysis Adsorptive: N2
   Analysis Bath:  77.30 K
Thermal Correction: No
Smoothed Pressures: No
  Cold Freespace:  53.0273 cm³
  Low Pressure Dose: 5.00 cm³/g STP
```

FIG. 2C

Figure 2C: Horvath-Kawazoe differential pore volume plot with slit pore geometry for the sample prepared according to example 2.

```
         Started: 03/18/99 11:49:36
       Completed: 03/20/99 02:27:11
     Report Time: 07/14/99 09:17:34
   Sample Weight: 0.3600 g
  Warm Freespace: 17.3334 cm³
  Equil. Interval: 10 secs
Analysis Adsorptive: N2
   Analysis Bath: 77.30 K
Thermal Correction: No
Smoothed Pressures: No
  Cold Freespace: 53.0273 cm³
Low Pressure Dose: 5.00 cm³ /g STP
```

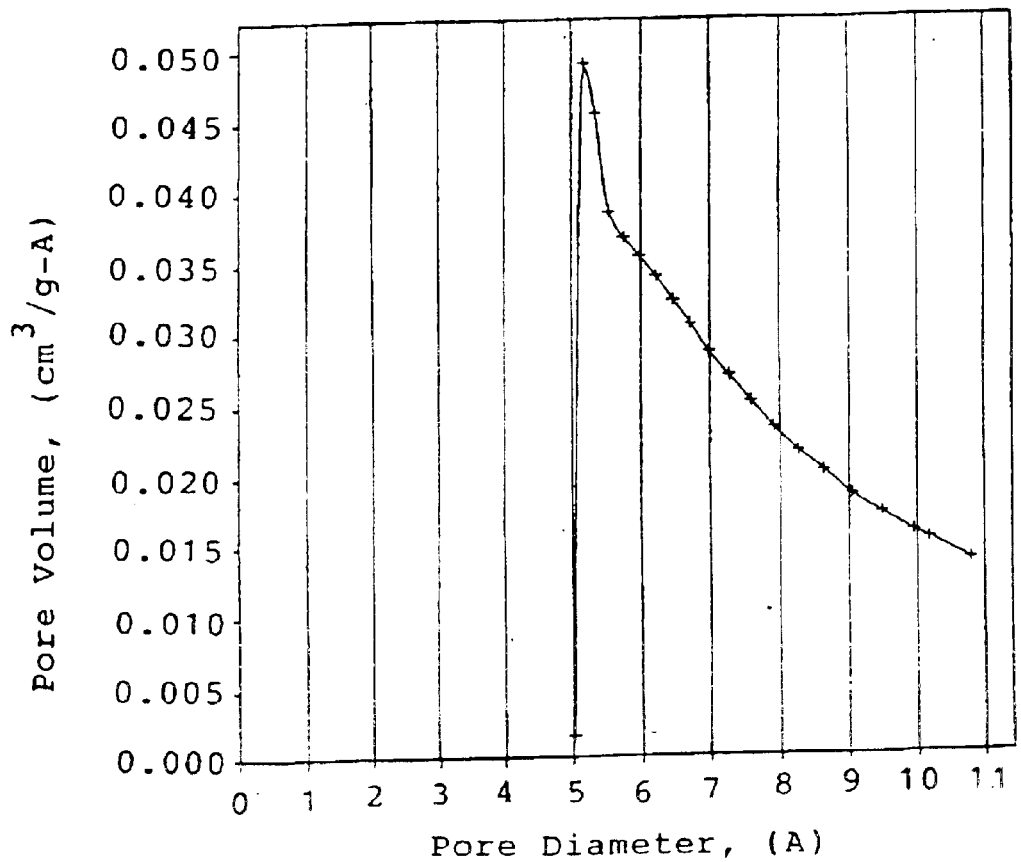

Horvath-Kawazoe Differential Pore Volume Plot
Slit Pore Geometry (original HK)

Example 3

Example 4

Figure 3B: BJH Desorption dV/dlogD curve for the sample prepared according to example 3.

```
          Started: 03/15/99 15:50:42
        Completed: 03/17/99 07:17:44
      Report Time: 04/05/99 14:41:11
    Sample Weight: 0.2140 g
   Warm Freespace: 18.3702 cm³
   Equil. Interval: 10 secs
Analysis Adsorptive: N2
    Analysis Bath: 77.30 K
Thermal Correction: No
Smoothed Pressures: No
   Cold Freespace: 56.4418 cm³
 Low Pressure Dose: 5.00 cm3 /g STP
```

FIG. 3C

Figure 3C: Horvath-Kawazoe differential pore volume plot with slit pore geometry for the sample prepared according to example 3.

| | |
|---:|:---|
| Started: | 03/15/99 15:50:42 |
| Completed: | 03/17/99 07:17:44 |
| Report Time: | 07/14/99 13:57:02 |
| Sample Weight: | 0.2140 g |
| Warm Freespace: | 18.3702 cm$^3$ |
| Equil. Interval: | 10 secs |
| Analysis Adsorptive: | N2 |
| Analysis Bath: | 77.30 K |
| Thermal Correction: | No |
| Smoothed Pressures: | No |
| Cold Freespace: | 56.4418 cm$^3$ |
| Low Pressure Dose: | 5.00 cm3 /g STP |

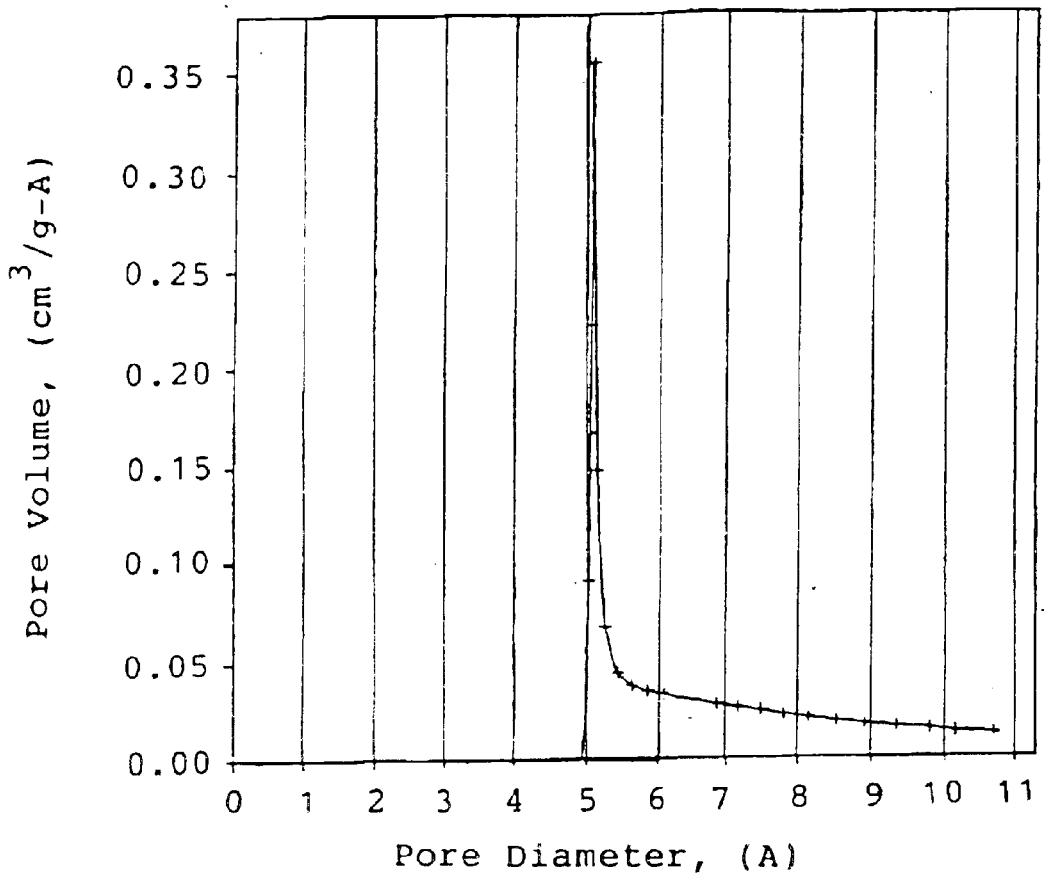

Horvath-Kawazoe Differential Pore Volume Plot
Slit Pore Geometry (original HK)

Example 5

Example 6

Figure 5B: BJH Desorption dV/dlogD curve for the sample prepared according to example 5.

```
         Started: 07/26/99 11:03:10
       Completed: 07/27/99 23:22:25
     Report Time: 07/29/99 16:21:36
   Sample Weight: 0.1220 g
   Warm Freespace: 18.1883 cm³
  Equil. Interval: 10 secs
Analysis Adsorptive: N2
   Analysis Bath: 77.30 K
Thermal Correction: No
Smoothed Pressures: No
   Cold Freespace: 55.4195 cm³
  Low Pressure Dose: 5.00 cm³ /g STP
```

FIG. 5C

Figure 5C: Horvath-Kawazoe differential pore volume plot with slit pore geometry for the sample prepared according to example 5.

```
           Started: 07/26/99 11:03:10
         Completed: 07/27/99 23:22:25
       Report Time: 07/29/99 16:21:36
     Sample Weight: 0.1220 g
    Warm Freespace: 18.1883 cm³
    Equil. Interval: 10 secs
 Analysis Adsorptive: N2
      Analysis Bath: 77.30 K
 Thermal Correction: No
  Smoothed Pressures: No
    Cold Freespace: 55.4195 cm³
  Low Pressure Dose: 5.00 cm³/g STP
```

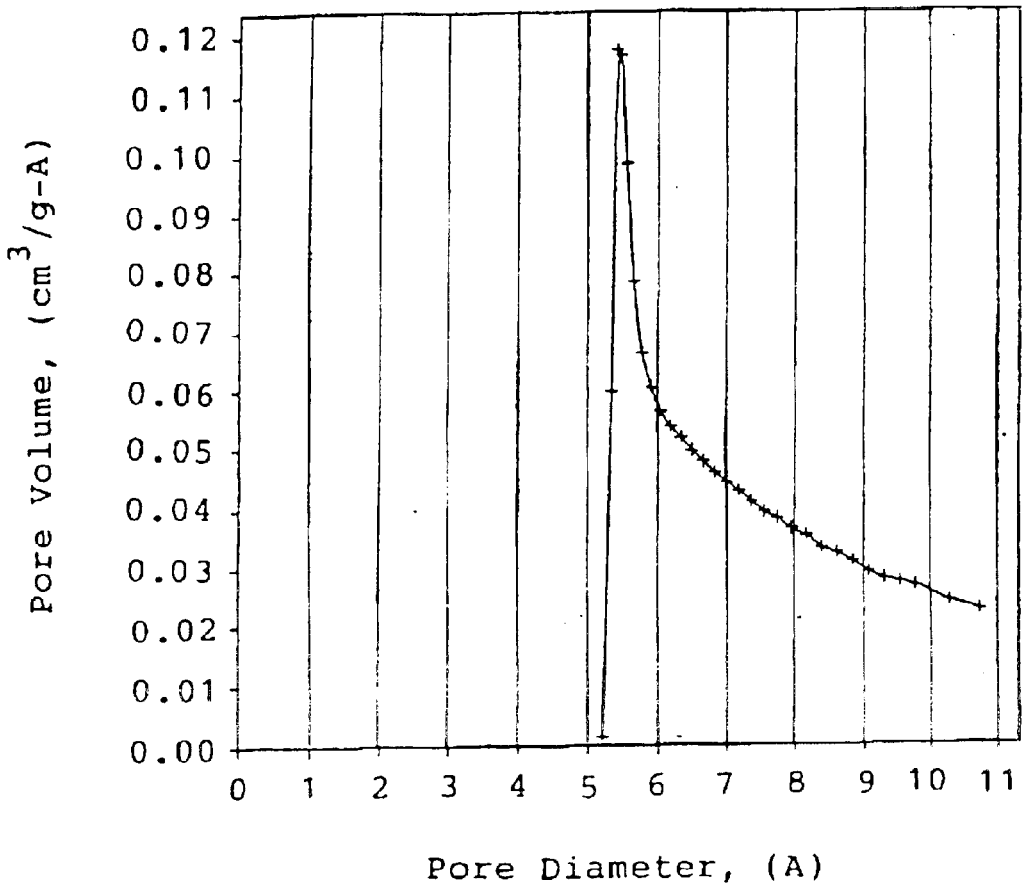

Horvath-Kawazoe Differential Pore Volume Plot
Slit Pore Geometry (original HK)

XRD patterns of (a) pure beta zeolite, (b) beta-TUD-1 and (c) high-resolution measurement of beta-TUD-1.

Transmission Electron Microscopy image of
the material made in Example 8.

Micropore size distribution of beta-TUD-1.

$NH_3$-TPD of beta-TUD-1 and all-silica mesoporous product as produced in Example 2 ("TUD-1").

Transmission Electron Microscope photograph of the material produced in Example 3.

INORGANIC OXIDES WITH MESOPOROSITY OR COMBINED MESO- AND MICROPOROSITY AND PROCESS FOR THE PREPARATION THEREOF

This application is a continuation-in-part of U.S. application Ser. No. 09/390,276, filed on Sep. 7, 1999 now U.S. Pat. No. 6,358,486.

The invention is directed to inorganic oxide materials having mesopores as well as micropores, or mesopores with a reduced amount of micropores or micropores with a reduced amount of mesopores and to a process for the preparation thereof.

Zeolites and related materials possess well-arranged pore systems and display uniform pore sizes. However, these materials tend to possess either only micro- or only mesopores. Furthermore these materials are rather expensive to produce.

There is a need for inorganic materials and in particular catalytic materials (or catalytic supports) that include both meso- and micro-pores.

There is also a need for new procedures for producing inorganic materials that contain mesopores and/or micropores.

Accordingly, in accordance with the invention, there is provided an inorganic oxide material having a pore structure, wherein at least part of its pores are in the mesopore size range and a part are in the micropore size range, and a method for producing such material as well as materials that contain essentially only mesopores (less than three volume percent and generally less than two volume percent of micropores) in an easy, inexpensive, and reproducible manner.

Furthermore, it is an object of the present invention to provide a silicate material that can easily be modified to have advantageous properties, such as specific catalytic properties, for example, by replacing part of the silicon atoms by metal atoms such as aluminium, titanium, vanadium, gallium, iron and the like. Other objects and advantages will become clear from the subsequent description.

In accordance with an aspect of the invention, inorganic oxides that include micropores and mesopores can be prepared in an easy and simple manner by the use of certain compounds, resulting in materials having advantageous properties, such as specific pore structure, high pore volume and the ability to be modified, both on the surface and in the material itself.

In one embodiment, the material of the invention is an inorganic oxide (preferably a silicate), having a bimodal structure of micropores and mesopores, domains of said micropores being connected to said mesopores, wherein the average mesopore size, determined by $N_2$-porosimetry, is between 2 and 25 nm, and the average micropore size, determined by $N_2$-porosimetry, is between 0.4 and 2.0 nm, preferably between 0.5 and 1.5 nm.

In accordance with one aspect of the present invention, the mesopores of the material have a defined pore size distribution. More particularly, the pore size distribution of the mesopores is such that in a pore size distribution plot wherein the derivative of pore volume is plotted on the y-axis and the pore diameter is plotted on the x-axis, in such a plot, the ratio of the width of the plot at the point of the y-axis which is one-half of the height of the plot, to the pore diameter at the maximum height of the plot is no greater than 0.75 and is preferably no less than 0.01. More preferably such ratio is no greater than 0.5.

Figure 1A:
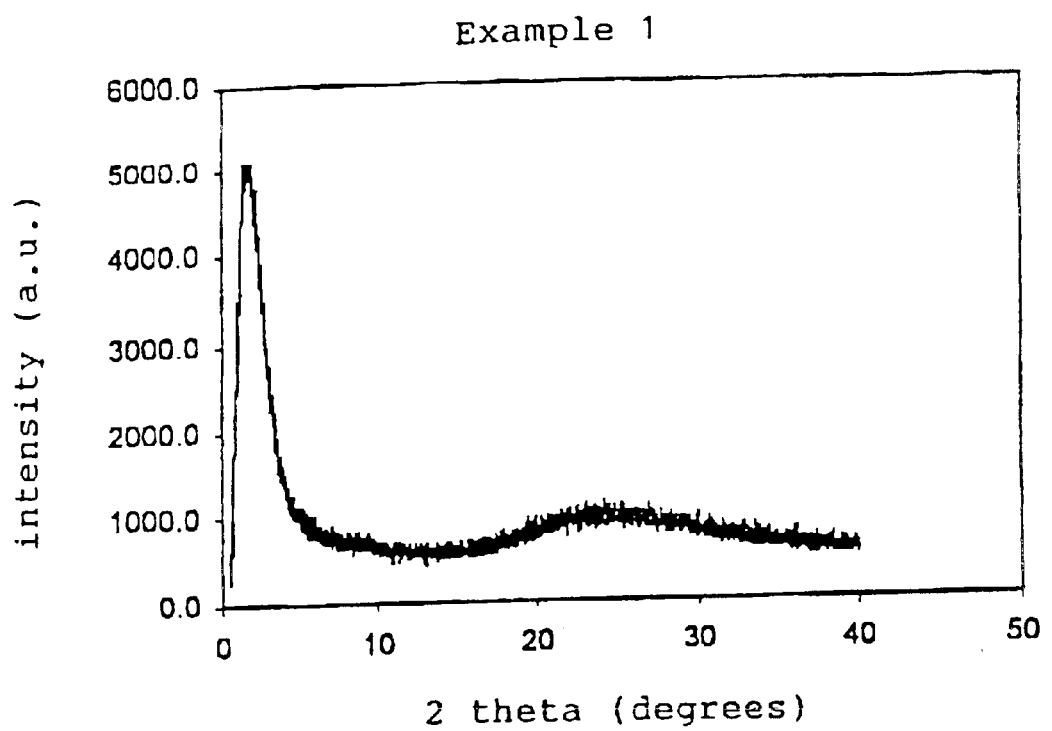
FIG. 1 is an x-ray pattern of material produced in Example 1.
FIG. 1B is a plot of the derivative of pore volume as a function of pore diameter for the micropores of the material of Example 1.
FIG. 1C is a plot of the derivative of pore volume as a function of pore diameter for the mesopores of the material of Example 1.

The bimodal inorganic material that includes both mesopores and micropores generally includes at least 3 volume percent of micropores (preferably at least 5%) and generally does not include more than 60 volume percent of micropores (preferably no greater than 50%), with such volume percents being based on the combined volume of mesopores and micropores.

In accordance with an aspect of the present invention, there is provided an inorganic oxide that includes both mesopores and micropores, which is prepared by heating a mixture of (1) an inorganic oxide in water, and (2) an organic material that mixes well with the oxide, and preferably forms hydrogen bonds with it. Optionally, the mixture may also include a template of the type that is used for producing micropores in forming molecular sieves (in particular, zeolites) said heating being at temperature levels and for a time sufficient to produce a silicate that contains both mesopores and micropores. Optionally, the mixture may include a preformed crystalline zeolite, in finely divided form to introduce a crystalline microporous phase and to aid in the production of a microporous crystalline structure in accordance with the invention.

The starting material is generally an amorphous material and may be comprised of one or more inorganic oxides such as silicon oxide or aluminum oxide with or without additional metal oxides. The additional metals may be incorporated into the material prior to initiating the process for producing a structure that contains mesopores and micropores and/or metal may be added to the preparation that is employed for producing an inorganic oxide that contains both micro- and mesopores.

The organic compound(s) that bind(s) to the inorganic oxide by hydrogen bonding is preferably a glycol (a compound that includes two or more hydroxyl groups), or member(s) of the group consisting of triethanolamine, sulfolane, tetraethylene pentamine and diethylglycol dibenzoate.

The template or micropore forming agent that may be combined with the material that hydrogen bonds to the inorganic oxide is of the type that is generally used for producing molecular sieves or zeolites from silicates. Such templates are generally known in the art.

In general, the templating agent for producing micropores may be an organic compound that contains an element of Group VA of the periodic Table of Elements, particularly nitrogen, phosphorus, arsenic and antimony, preferably N or P and most preferably N. The compounds also contain at least one alkylene, alkyl or aryl group having from 1 to 8 carbon atoms. Particularly preferred nitrogen-containing compounds for use as templating agents are the amines and quaternary ammonium compounds, the latter being represented generally by the formula $R_4 N^+$ wherein R is an alkyl or aryl group containing from 1 to 8 carbon atoms, or mono-, di- and triamines, either alone or in combination with a quaternary ammonium compound or another templating compound. Illustrative organic templating agents are the following: tetramethylamonium ("TMA"), tetraethylammonium ("TEA"), tetra-n-propylammonium ("TPA"), tetra-isopropylammonium and tetrabutylammonium salts, di-n-propylamine, di-n-butylamine, tri-n-propylamine, triethylamine, tributylamine, quinuclidine ("Q"), methyl quinuclidine hydroxide, cyclohexylamine, neopentylamines, N,N-dimethylbenzylamine, N-N-dimethylethanolamine, di-n-pentylamine, isopropylamine, t-butylamine, ethylenediamine; hexamethylene-diamine, pyrrolidine; 2-imidazolidone, piperidine, 2-methylpyridine, N,N'-dimethylpiperazine, N-methyldiethanolamine, N-methylethanolamine, N-methylpiperidine, 3-methylpiperidine, N-methylcyclohexylamine, 3-methylpyridine, 4-methylpyridine, diethylpiperidinium ("DEPP"), trimethylbenzylammonium ("TMBA"), tetramethylphosphonium ("TMP"), 5-azoniaspiro(4,4)nonane or bispyrrolidinium ("BP"), (2-hydroxyethyl)trimethylammonium ("choline"), 1,4-dimethyl-1,4-diazoniabicyclo(2,2,2)octane ("DDO"), 1,4-diazoniabicyclo (2,2,2)octane ("DO" or "DABCO"), N,N'-dimethyl-1,4-diazabicyclo (2.2.2) octane ion, etc.

Although a template of the type used for producing a molecular sieve with micropores may be used in the present invention in conjunction with the hydrogen bonding material, and such materials in many cases are known to produce a crystalline structure, when used in the present invention, such templates may give rise to the formation of micropores while not producing a crystalline structure. On the other hand, if a crystalline structure is formed, it may not be detectable by X-ray diffraction, due to the limited size of the microporous domains. However, these microporous domains may measurably affect the acidity of the material. If a preformed zeolite phase is added, the microporous domains are sufficiently large to be detected by X-ray diffraction. In many cases, the resulting inorganic oxide that includes both micro-pores and meso-pores is a pseudo crystalline material that includes an ordered or regular structure in a three-dimensional pattern without being crystalline.

Without limiting the present invention, it is believed that the material that binds to the inorganic oxide by hydrogen bonding (alone or in combination with the "template") causes the oxide to form a thin-walled structure having mesopores. The micropores will be homogeneously dispersed within the walls of the mesoporous structure.

The material of the invention is accordingly a mesoporous inorganic oxide material or a mesoporous-microporous inorganic oxide material (preferably a silicate), which optionally may contain metal ions of groups IVB–IIB and IIIA, such as aluminium or titanium, as part of the mesoporous structure, either added during the preparation and incorporated directly during synthesis, or which may be introduced into the lattice by exchange with the metal ions that are present in the lattice after production. Depending on the nature of the other metal ions the properties of the material differ. For example, by incorporating aluminium in silicates, it is possible to give the material acidic properties, whereas some other metals may result in alkaline properties, thus making it useful as an oxidation catalyst.

The material has interconnected mesopores, with a pore diameter between 2 and 25 nm. The mesopores are believed to be formed by cages having a kind of "sausage structure". The pores have a somewhat spherical shape, generally with two or more connections to other pores at two opposite ends thereof. Evidence of this type of structure is found by Transmission Electron Microscopy imaging of the material, see Example 3. On the other hand, the material may also contain domains or phases of micropores, which are connected to the mesopores. Thus, in accordance with an aspect of the present invention, there is provided a one-step method to produce a bimodal pore system.

In the bimodal inorganic material of the present invention, there is a distinct peak of micropores and a distinct peak of mesopores in a plot of the derivative of pore volume against pore size. In general, in a Horvath-Kawazoe plot the width of the micropore peak at half-height is no greater than 2 angstroms and generally no greater than 1 angstrom.

The mesoporous and mesoporous-microporous materials according to one embodiment of the invention are a pseudo-crystalline material (no crystallinity is observed by presently available x-ray diffraction techniques). According to one embodiment the materials have one peak in the XRD diffraction pattern, where 2θ is between 0.5 and 2.5°. The presence of one peak means that the material has an extremely regular structure, without being crystalline. Said regular structure is determined by a distribution of wall thicknesses, in combination with a narrow distribution of the sizes of the mesopores. The wall-to-wall distance of the mesopores will preferably be between 3 and 25 nm.

In another embodiment, the mixture from which the bimodal material is to be produced also includes a crystalline zeolite, in finely divided form. The objective of this procedure is to maintain the structure of the crystalline zeolite and to obtain a well-dispersed zeolite phase in the mesoporous structure. The presence of the crystalline zeolite may aid in producing a crystalline structure in the micropores.

The zeolite may be formed from the same material from which the inorganic oxide material is to be produced or the zeolite may be comprised of a different material.

The zeolite included in the starting mixture generally has an average particle size of from 5 to 1500 nanometers. Such materials are known in the art and may be produced by procedures known in the art.

The crystalline zeolite is suspended in water and the other components are added thereto; in particular, the inorganic oxide and the compound that binds to the inorganic oxide by hydrogen bonding.

Such mixture may or may not include a templating agent of the type generally used for producing zeolites. The type and concentration of the templating agent needs to be chosen in order to prevent breakdown of the added zeolite. The mixture that contains a zeolite is preferably maintained at a pH of less than 11.4, although, in some cases, a higher pH could be used. Moderate pH conditions minimize the breakdown of the zeolite structure during the synthesis of the mesoporous or bimodal structure. On the other hand the pH is preferably higher than 8, in order to obtain sufficiently high gelation rates. Gelation ultimately increases the viscosity of the synthesis mixture.

The mixture is generally maintained with stirring (for example, at room temperature) until the viscosity reaches a value that prevents the finely divided zeolite from settling out of the mixture.

By including a crystalline zeolite in the starting mixture and preventing breakdown of the zeolite structure, at least a portion of the micropores have a crystalline structure.

The material having a bimodal pore structure is suitable for carrying out all kinds of chemical reactions which require, on the one hand, large pores and, on the other hand, small pores. Examples thereof are reactions where large molecules can easily enter the system via the mesopores and are then reacted or converted in the micropores. This may result in selective reactions. The material intrinsically has a high surface area in combination with large pores that result in high accessibility and consequently high intrinsic volumetric activity. Another advantage of creating ordered microdomains in the walls of the mesoporous structure is the possibility of introducing catalytic sites with higher acid strength than hitherto possible in purely mesoporous materials.

Another example of the suitability of the materials is in petroleum chemistry, wherein large molecules are first converted in the mesopores into smaller molecules which subsequently reacted in the micropores. In this way, one may get very controlled and selective conversion of, for example, oil fractions.

The inorganic oxide may consist of silicon and oxygen only. Part of the silicon may be replaced by another metal, preferably by adding a source of said metal during the preparation of the material. Examples of suitable metals are titanium, vanadium, zirconium, gallium, manganese, zinc, iron and aluminium.

Furthermore, it is possible to exchange, after preparation of the material, cations in the system with other ions, such as those of an alkali metal. In this manner, carefully controlled properties can be generated. For example, the presence of titanium as an additional component in silicate creates additional catalytic properties (for example, oxidation properties) on the internal surface of the material, which may be a very interesting feature, especially in fine chemistry.

The material, according to the invention, generally has an average surface area as determined by BET ($N_2$) of between 400 and 1200 $m^2/g$. The combined micro- and mesopore volume in the bimodal material or the mesopore volume in the monomodal mesoporous material determined by nitrogen absorption will generally be between 0.3 and 2.2 ml/g.

An important advantage of the materials of the present invention is the stability thereof. It has been found that the material is more stable than the standard mesoporous materials, such as MCM-41 of Mobil. This stability is determined in terms of decrease of intensity of the most important peak in XRD, pore volume and pore size after treatment of the material in boiling water, for example, for about 2 hours.

More in particular, the material is prepared by a process which comprises providing an aqueous phase having dispersed therein an inorganic oxide precursor, such as a silica source. Preferably, this is a solution of a suitable silicate. Generally, the pH of the aqueous phase will preferentially be above 7. Optionally, the aqueous phase may contain other metal ions such as derivable from an aluminium salt. The aqueous phase also includes an organic material that binds to the silicate, in particular, by hydrogen bonding which aids in the formation of the mesopores. The material that binds to the silica should not be too hydrophobic so as to form a separate phase. Finally, it is advantageous if such material has a relatively high boiling point, such as at least 150° C. Examples of suitable materials are triethanolamine, sulfolane, tetraethylenepentamine, diethylglycoldibenzonate or glycols (compounds that have two or more hydroxyl groups), such as glycerol, diethylene glycol, triethylene glycol and tetraethylene glycol. To achieve good mixing between the inorganic oxide precursor solution and the aqueous hydrogen bonding compound/template mixture, drop-wise addition of the template/hydrogen bonding compound solution to the inorganic oxide phase is preferred. The addition rate is generally between 2 and 20 g/min. and preferably between 3 and 8 g/min.

If micropores are to be introduced into the mesoporous phase, a micropore forming agent is preferably added of the type used for producing micropores in zeolite production. Alternatively, the mixture may include a crystalline zeolite, in finely divided form On the other hand, the mixture may include a combination of a micropore forming agent and a crystalline zeolite.

In a preferred embodiment, the mixture also includes an alcohol, preferably an alkanol. The alcohol may be added to the mixture or may be produced by decomposition of the material that is used as the source of the metal oxide. For example, when using tetraethyl orthosilicate as a source of silica, upon heating, ethanol is produced, or when using aluminum isopropoxide as a source of alumina, propanol is produced. Thus, in a preferred embodiment, an alcohol may be included in the mixture or generated from one of the materials used during the process.

Depending on the type of inorganic oxide source, the synthesis mixture may be first aged at a temperature, for example, from 5° C. to 45° C.; e.g., at room temperature, for a period, to expel any organic compounds from the inorganic oxide source (such as from tetraethyl orthosilicate), for example, up to 48 hrs. If a zeolite is added to the synthesis mixture, aging is extended up to the point at which the viscosity of the mixture has increased sufficiently to prevent settling of the zeolite particles. As discussed hereinabove, an increase of the pH by addition of e.g. an organic base to the synthesis mixture increases gelation rates during the aging step. On the other hand, breakdown of the zeolite phase in subsequent steps should be prevented by limiting the pH. In a preferred embodiment, the pH is between 9 and 11.4.

After the aging stage, the material is subsequently gradually heated to about the boiling point of water. Thereby the water and the organic components generated from the inorganic oxide source (such as methanol or ethanol) evaporate. In order to obtain a product with the desired high integrity, it is preferred to achieve a homogeneous heating rate and the absence of a temperature profile in the precursor phase during this drying step. This is achieved by maximizing the heat transfer surface area of the gel during the evaporation, e.g., by using shallow beds, breaking up the solid phase after drying, or by using rotary evaporators. During this drying stage, the organic molecules that aid in forming the micro and mesopores should not be removed from the system to a substantial degree. Accordingly, the organic material that binds to the inorganic oxide should preferably have a boiling point above, at least, 150° C. The drying may take, for example, 6 to 48 hrs.

After the drying stage to remove water, which is maintained, for example, for about 6 to 48 hours the inorganic oxide, which still contains the mesopore forming agent, is heated to a temperature at which there is substantial production of mesopores; i.e., a temperature above the boiling point of water and up to the boiling point of the mesopore forming agent. The temperature of the system may be increased to a calcination temperature, for example, temperatures of from 300° C. to 1000° C., preferably at least 400° C., and maintained at such temperature for a time sufficient to effect such calcination of the material. To prevent hot spots, the heating rate should be sufficiently low and the height of the sample bed should be limited. The heating rate during calcination is preferably between 0.1 and 25° C./min., more preferably between 0.5 and 15° C./min., and most preferably between 1 and 5° C./min. The material may be subjected to hydrothermal treatment prior to drying or after drying and prior to calcination, e.g., in a sealed vessel at autogenous pressure and at temperatures above 100° C. and which generally do not exceed 350° C. The size of the mesopores and the volume of micropores in the final product are influenced by the length and temperature of the hydrothermal step. In general, it is observed that in the final product the percentage of mesopores increase and the percentage of micropores decrease with increasing temperature and increasing duration of the hydrothermal treatment. Preferably, to maintain micropore volume the hydrothermal step is not used. It is also possible to extend the hydrothermal treatment such that the micropore volume becomes negligible and the material contains essentially only mesopores.

It is within the scope of the invention to remove the molecules that are the templates for the mesopores from the inorganic oxide, prior to reaching a temperature at which mesopores are substantially formed, for example, by extraction which leads to the formation of a material with pores smaller than 20 Å, which also contains mesopores; however, there is no distinct peak of mesopores when a plot is prepared of the derivative of pore volume against pore size. For example, mesopores are not substantially formed at temperatures below 100° C.; however, it may be possible to heat to temperatures somewhat in excess of 100° C. without mesopore formation.

During the calcination, the structure of the material is finally formed, while furthermore the organic molecules are expelled from the system and can be recovered for re-use. If necessary, the material may be washed, although generally the type of components are such that no washing is necessary, as no additional components will be present in the system. Due to this method of preparation, no waste water is produced. A further advantage of the invention resides therein, that the preparation method is highly efficient, due to the 100% utilization of the silica and the possibility of recovery of the organic compounds.

If necessary, further steps may be taken to add metal ions such as titanium, vanadium, zirconium, gallium, manganese, zinc, nickel, cobalt, chromium, molybdenum, or iron by impregnation, ion exchange, or by replacing part of the lattice atoms, as described in G. W. Skeels and E. M. Flanigen in M. Occelli, et al., eds., A.C.S. Symposium Series, Vol. 398, Butterworth, pgs. 420–435 (1989). For silicate structures, it also is possible to treat the surface layer of the inside of the pores in such a manner that the silicate material is converted to a zeolitic structure, e.g., by impregnation with an aqueous solution of a template. In this manner, one has obtained, with a bimodal pore size, a material having pores with a zeolitic inside structure. This may be done by "skin modification," which means that a suitable metal or template ion is positioned in the wall, followed by a heat treatment. This method of skin modification has been disclosed in the plenary lecture "Zeolite Coatings" by J. C. Jansen, at the $12^{th}$ IZC, Baltimore, July 1998 (Proc. 12th IZC Baltimore, M.M.J. Treacy et al eds., MRS Warrendale (PA), (1999), 1, 603–611) and in the references cited in this lecture.

Also, it is possible to adapt the properties of the material with a catalytically active material such as a precious metal, by impregnation or by a combination of ion exchange and reduction. Moreover, it also is possible to attach (graft) functional components on the wall by reaction of surface hydroxyl groups with the compound in the gas or liquid phase.

In the present description, mention has been made of micropore sizes and mesopore sizes. Micropores are defined as pores having a diameter of less than 2.0 nm. Mesopores are defined as pores in the range of 2 to 50 nm. The pore size distribution of materials prepared by the present invention may be determined by nitrogen adsorption and desportion and producing from the acquired data a plot of the derivative of pore volume as a function of pore diameter.

The nitrogen adsorption and desorption data may be obtained by using instruments available in the art (for example Micrometics ASAP 2010) which instruments are also capable of producing a plot of the derivative of pore volume as a function of the pore diameter. In the micro pore range, such a plot may be generated by using the slit pore geometry of the Horvath-Kawazoe model, as described in G. Horvath, K. Kawazoe, J. Chem. Eng. Japan, 16(6), (1983), 470. In the mesopore range, such plot may be generated by the methodology described in E. P. Barrett, L. S. Joyner and P. P. Halenda, J. Am. Chem. Soc., 73 (1951), 373–380.

In an embodiment of the invention, the pore size distribution of materials produced in the present invention, in the mesopore range, is such that a pore size distribution curve showing the derivative of pore volume (dV) as a function of pore diameter is such that at a point in the curve that is half the height thereof, the ratio of the width of the curve (the difference between the maximum pore diameter and the minimum pore diameter at the half height) to the pore diameter at the maximum height of the plot (as hereinabove described) is no greater than 0.75.

The invention will be further described with respect to the following examples; however, the scope of the invention is not limited thereby.

EXAMPLES

Example 1
Synthesis of Bimodal Silica-alumina

Figure 1B:
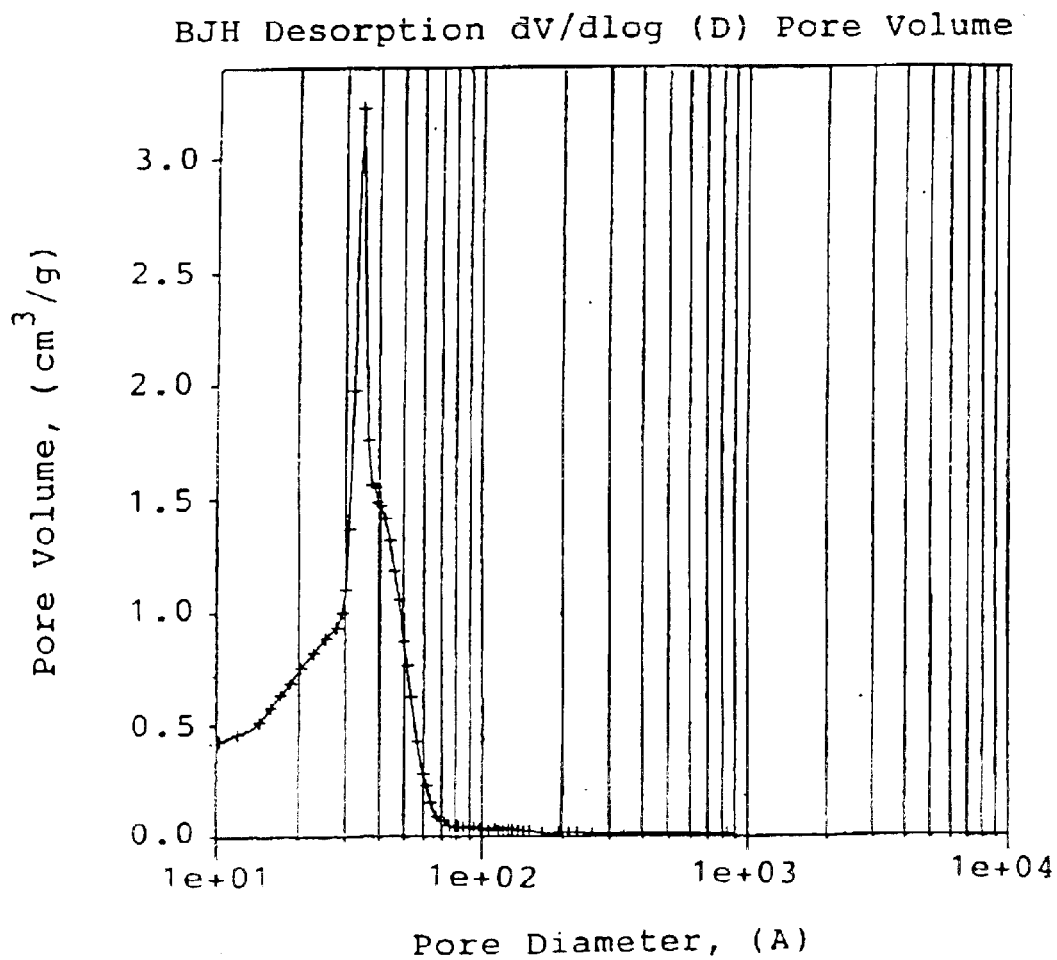

First, 1.3 g aluminium isopropoxide was dissolved in 39.1 g TPAOH tetrapropylammonium hydroxide (40%) aqueous solution. Next, 47.88 g triethanolamine (97%, ACROS) and 14.0 g water were mixed. The triethanolamine mixture was added drop-wise (8–10 g/min) to the aluminium containing mixture under stirring. Finally 33.1 g tetraethyl orthosilicate (98%, ACROS) was added drop-wise (4–6 g/min) to the resulting mixture while stirring. The final mixture was aged at room temperature for 48 h, spread out in a dish to form a layer that had a height of 1.0–1.2 cm and dried at 100° C. for 18 h in a static air furnace. The resulting material was calcined in air using the following procedure: with a heating rate of 1° C./min to 500° C., hold for 4 hours, with 1° C./min to 550° C., hold for 10 hrs. The X-ray pattern of the resulting product is shown in FIG. 1. The $N_2$ porosimetry results are given in Table 1.

Example 2
Synthesis of Bimodal Silica

Drop-wise addition of 17.37 g triethanolamine (75%, ACROS) took place at 4–6 g/min to a mixture of 94.72 g tetraethyl orthosilicate (98%, ACROS) and 136.87 g water under stirring. The homogeneous mixture was aged at room temperature for 16 h. The aged mixture was transferred to a dish to form a layer with a height of 1.8–2.0 cm and dried in a static air furnace of 100° C. for 24 hrs. Next the dried product was hydrothermally treated at 190° C. for 48 hrs. Calcination took place in air by heating at 1° C./min to 550° C. and holding for 10 hrs.

Figure 2A:
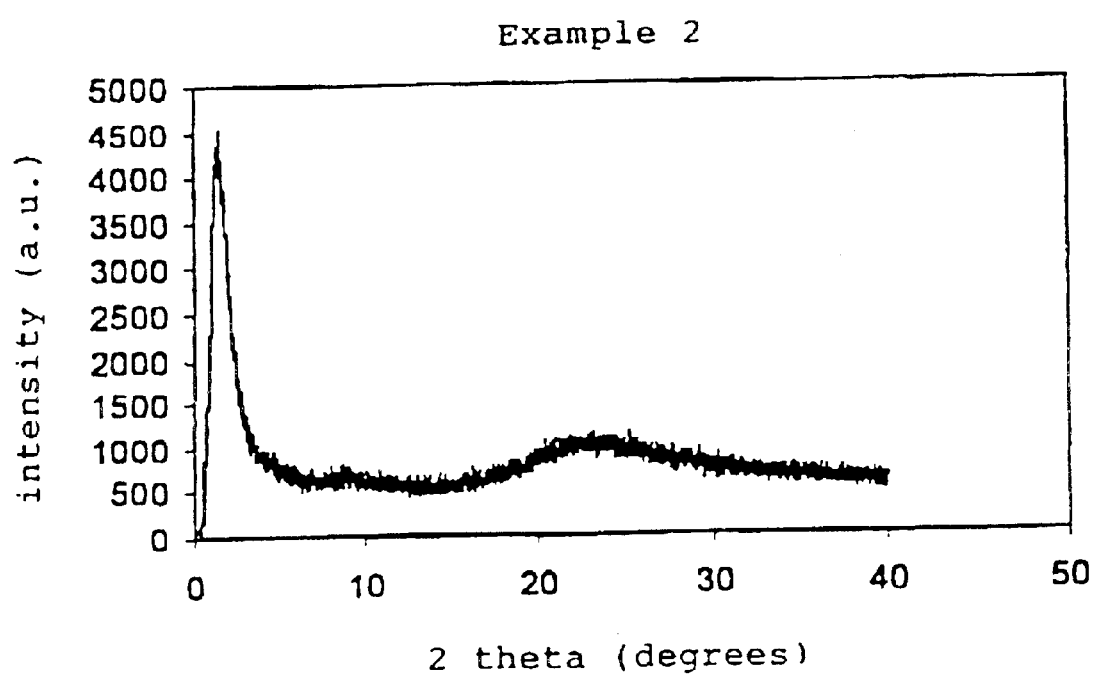
FIG. 2 is an x-ray pattern of material produced in Example 2.
FIG. 2B is a plot of the derivative of pore volume as a function of pore diameter for the micropores of the material of Example 2.
FIG. 2C is a plot of the derivative of pore volume as a function of pore diameter for the mesopores of the material of Example 2.
Figure 2B:
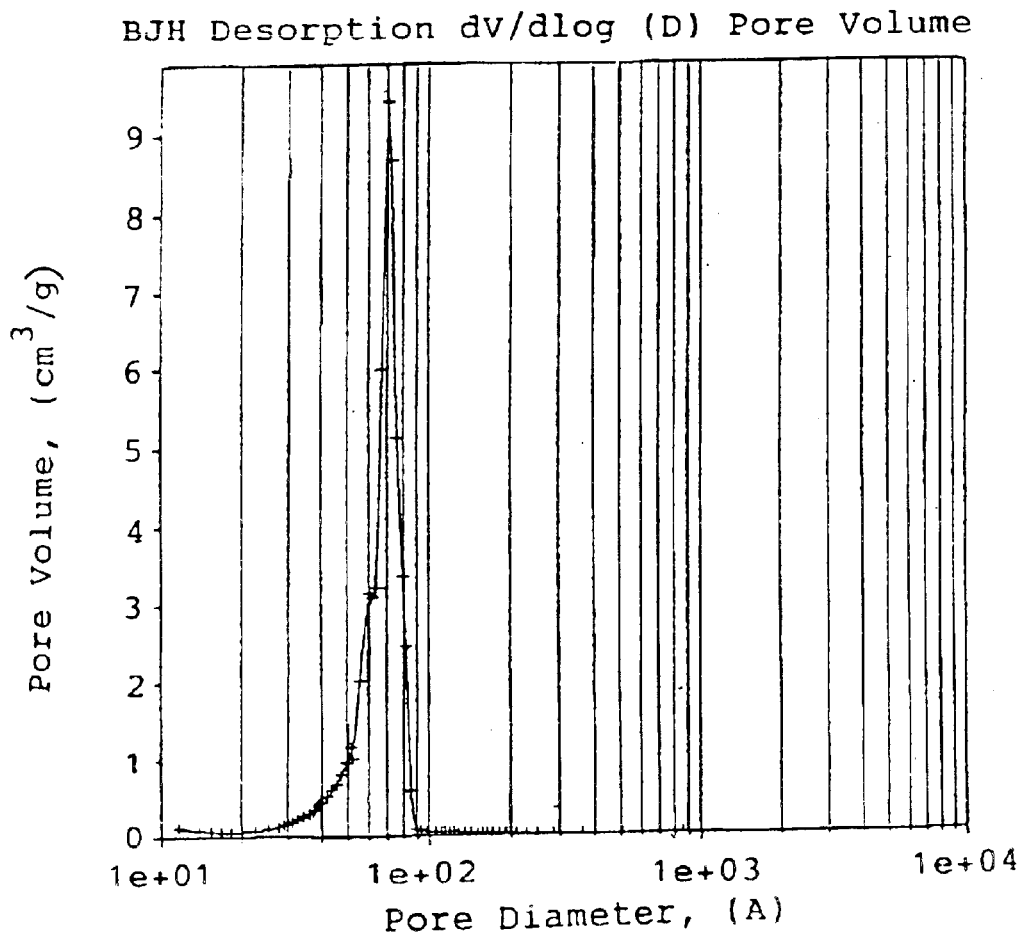

The X-ray diffraction pattern is given in FIG. 2. The nitrogen porosimetry results are given in FIG. 2B, 2C and Table 1.

Example 3
Synthesis of Bimodal Silica-alumina

Figure 3A:
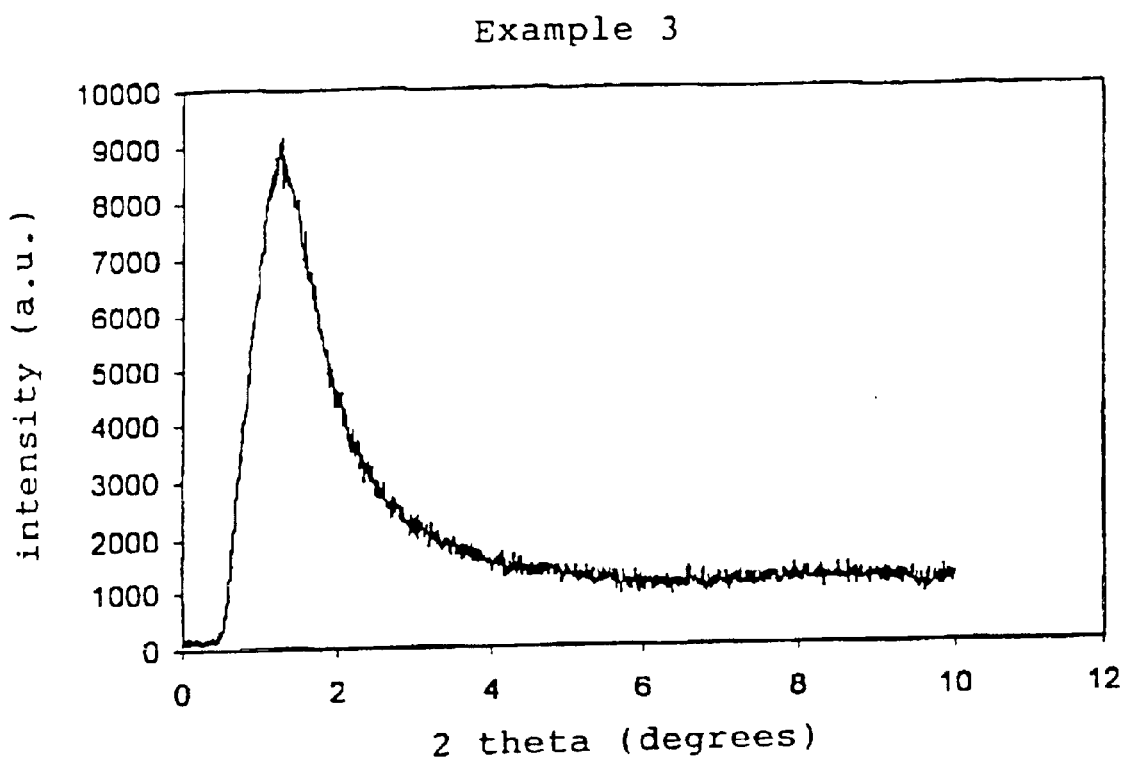
FIG. 3 is an x-ray pattern of material produced in Example 3.
FIG. 3B is a plot of the derivative of pore volume as a function of pore diameter for the micropores of the material of Example 3.
FIG. 3C is a plot of the derivative of pore volume as a function of pore diameter for the mesopores of the material of Example 3.
Figure 3B:
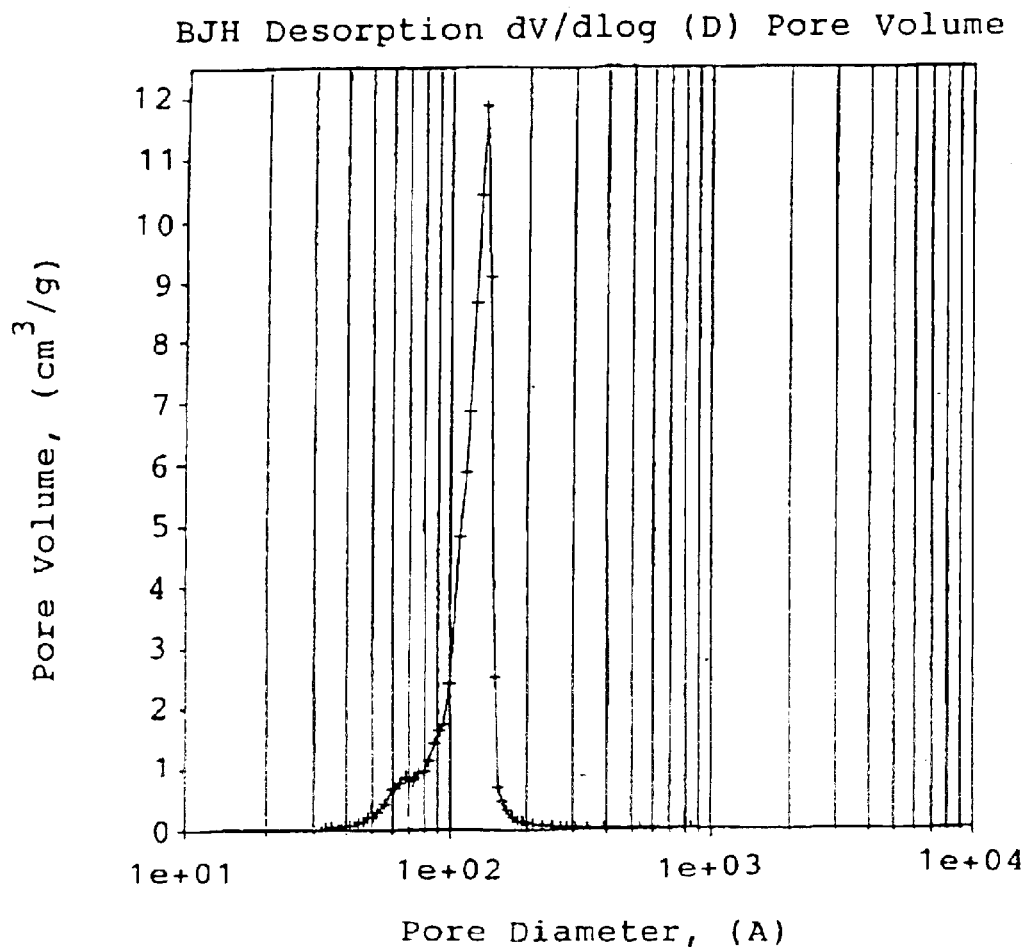
Figure 11:
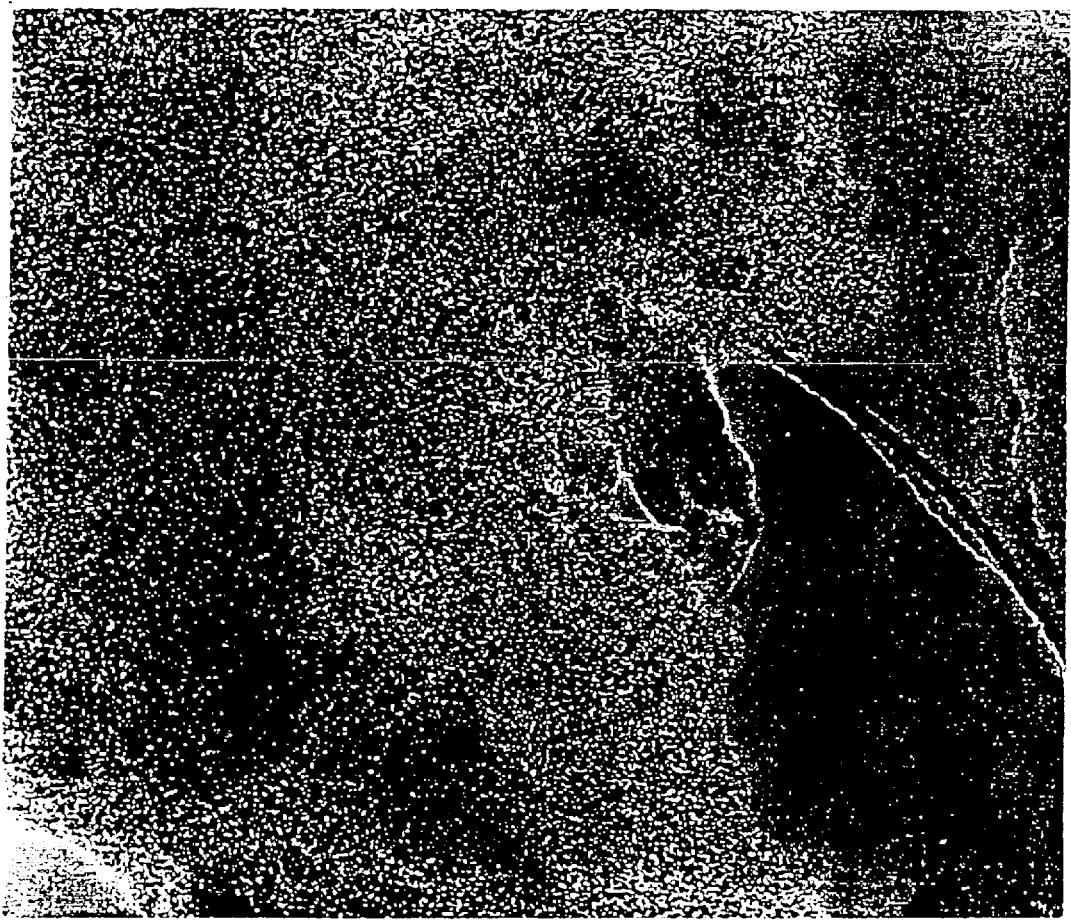
FIG. 11 is a Transmission Electron Microscopy image of the material produced in Example 3.

A mixture of 2.1 g of aluminium isopropoxide and 60.6 g isopropanol was made. To this mixture 53.06 g tetraethyl orthosilicate (98%, ACROS) was added drop-wise (8–10 g/min). Next, a mixture of 38.39 g triethanolamine (97%, ACROS) and 114.37 g water was added drop-wise (8–10 g/min) to the mixture above. Finally, 31.5 g tetraethyl ammonium hydroxide was added slowly (4–6 g/min) while stirring. The final mixture was aged at room temperature for 24 hrs. The mixture was transferred into a dish to form a layer with a height of 1.8–2.0 cm and dried in a static air furnace at 100° C. for 24 hrs. The dried product was hydrothermally treated at 190° C. for 24 hrs. Calcination took place in air at a heating rate of 1° C./min to 500° C., holding for 4 hrs. followed by heating at 1° C./min to 600° C. and holding for 10 hrs. FIG. 3 shows the X-ray diffraction pattern of the product. The $N_2$ porosimetry results are given in FIG. 3B, 3C and Table 1. A Transmission Electron Microscopy image of the structure is given in FIG. 11.

Example 4
Synthesis of Mesoporous Silica

Figure 4:
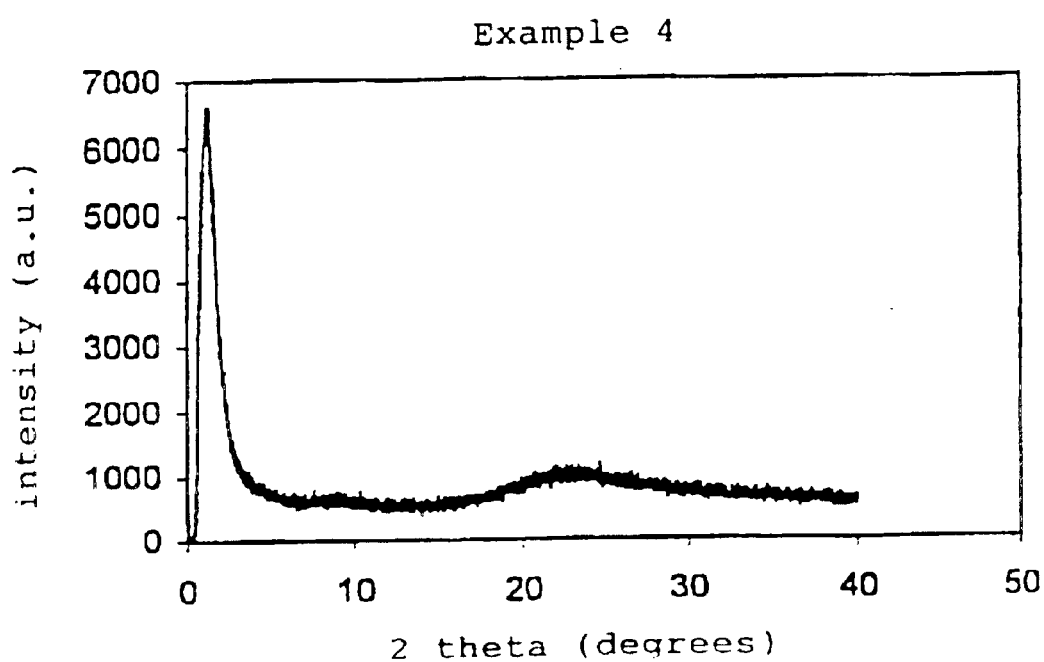
FIG. 4 is an x-ray pattern of material produced in Example 4.

A mixture of 29.12 g tetraethylene glycol (99%, ACROS) and 107.46 g water was added slowly (4–6 g/min) to 63.42 g tetraethyl orthosilicate (98%, ACROS) under stirring. The synthesis mixture was aged at room temperature for 22 hrs. The synthesis mixture was transferred to a dish to form a layer of approximately 1.8–2.0 cm and dried in a static air furnace at 100° C. for 24 hrs. Hydrothermal treatment took place in an autoclave at 190° C. for 24 hrs. The sample was calcined in air at 550° C. for 10 hrs. calcined with a heating rate of 1° C./min. FIG. 4 depicts the X-ray diffraction pattern of the product. The nitrogen porosimetry results are given in Table 1.

Example 5
Synthesis and Testing of Bimodal Ti-silicate

A mixture of 25.29 g triethanolamine, 17.29 g tetraethyl ammonium hydroxide (25%) and 18.01 g water was added drop-wise (4–6 g/min) into another mixture of 1.1 g titanium (IV) N-butoxide and 34.95 g TEOS under stirring. The final homogeneous mixture was aged at room temperature for 24 hrs. The mixture was transferred to a dish to form a layer of approx. 1.8–2.0 cm, and dried in a static air furnace at 100° C. for 24 hrs. The dried product was calcined at 600° C. for 10 hrs. with a ramp rate of 1° C./min in air.

Figure 5A:
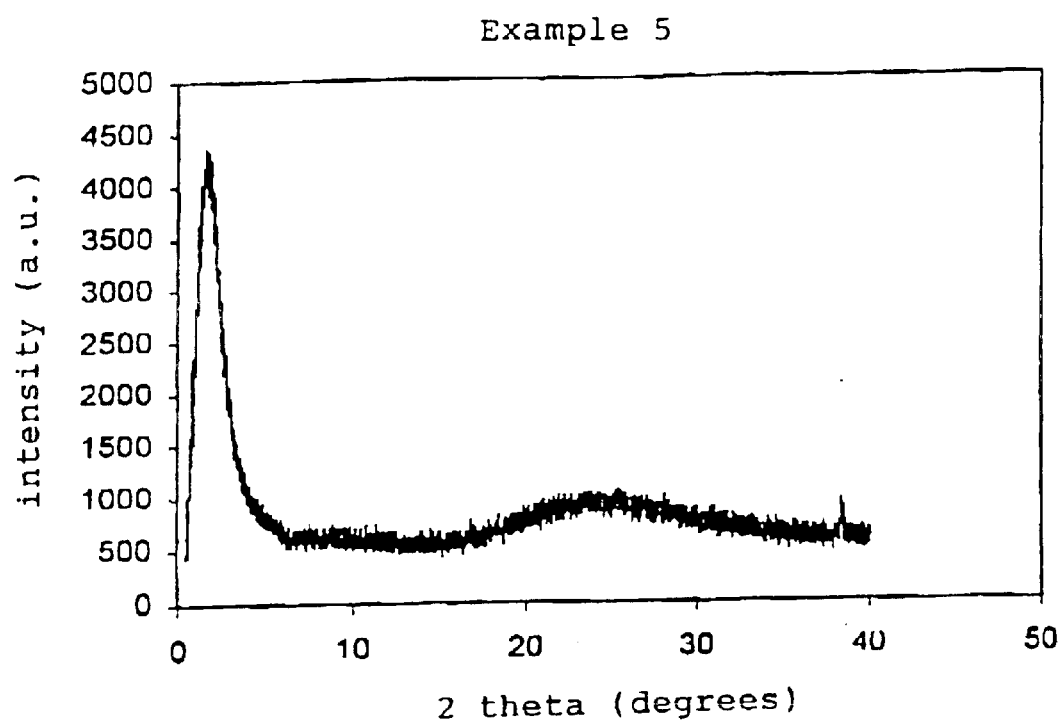
FIG. 5 is an x-ray pattern of material produced in Example 5.
FIG. 5B is a plot of the derivative of pore volume as a function of pore diameter for the micropores of the material of Example 5.
FIG. 5C is a plot of the derivative of pore volume as a function of pore diameter for the mesopores of the material of Example 5.
Figure 5B:
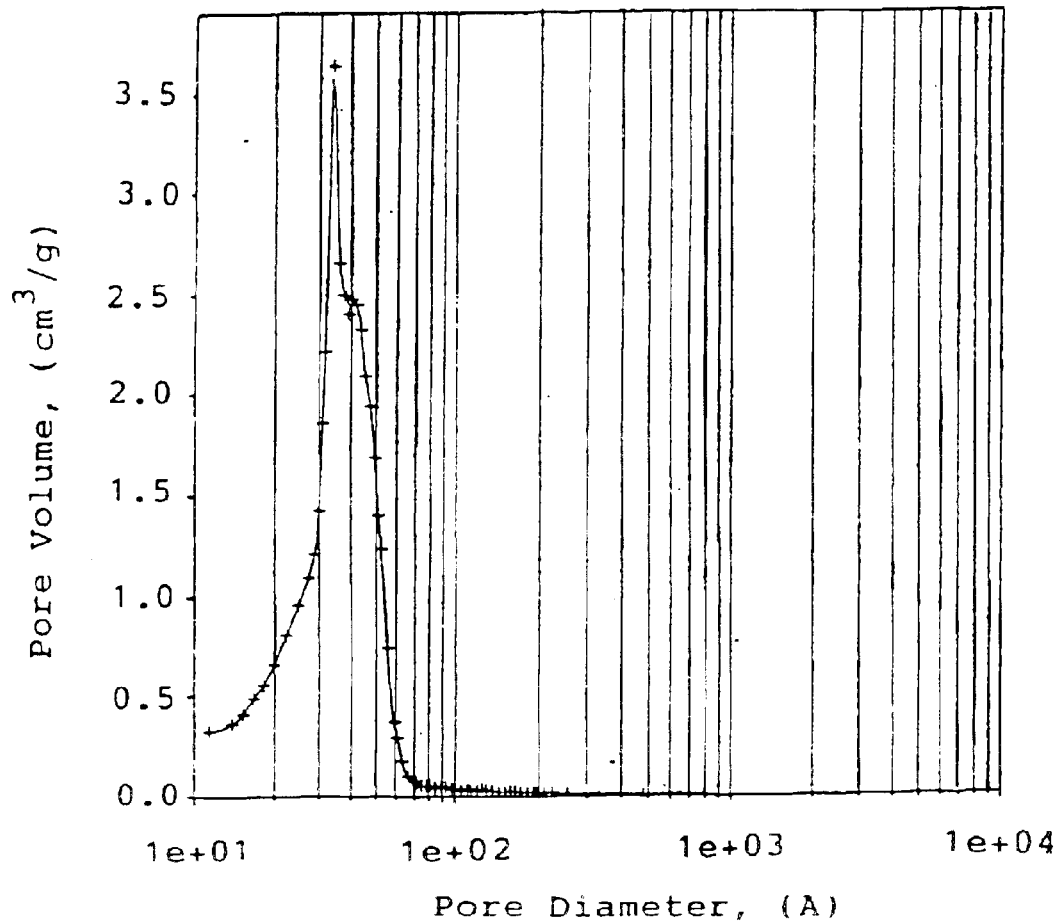

Its porosity was determined using nitrogen adsorption isotherm, which was measured at 77 K using the Micromeritics ASAP 2000. FIG. 5A shows the X-ray diffraction pattern of the product. The nitrogen porosimetry results are given in FIG. 5B, 5C and Table 1. Chemical composition was analyzed using Inductive Coupled Plasma-Atomic Emission Spectroscopy and it showed 1.65 wt % Ti.

Catalytic activity was evaluated using cyclohexene epoxidation as a model reaction, which was carried out at 40° C. under $N_2$ flow in a flask with a reflux condenser. Tert-butyl hydroperoxide (TBHP) (70% aqueous solution) as an oxidant was dried using anhydrous magnesium sulphate before use. 10 mmol cyclohexene (99%), 11 mmol TBHP was added into 10 ml of dichloromethane containing 5 mmol mesitylene as an internal standard. When the temperature reached 40° C., 0.11 g of the catalyst was introduced into the reactant mixture. Samples were analyzed by GC (WAX 52 CB). The turnover frequency, defined as moles of cyclohexene converted per mole of titanium per hour, reached 20.2 $h^{-1}$ after 6 hrs. This is about 5 times higher than over titanium containing MCM-41 under the same reaction conditions as described in C. H. Rhee, J. S. Lee, Catal. Lett., 1996, Vol. 40, 261–264.

Example 6
Synthesis of Mesoporous Silica 25.55 g tetraethyl orthosilicate (98%, ACROS) was added slowly (4–6 g/min) into a mixture of 17.37 g triethanolamine (97%, ACROS) and 56.98 g water under stirring. The obtained homogeneous synthesis mixture was aged at room temperature for 24 hrs. Next the mixture was transferred to a dish to form a layer of 1.8–2.0 cm height, and dried in a static air furnace at 100° C. for 18 hrs. The dried sample was calcined at 550° C. in air with a ramp rate of 1° C./min.

Figure 6:
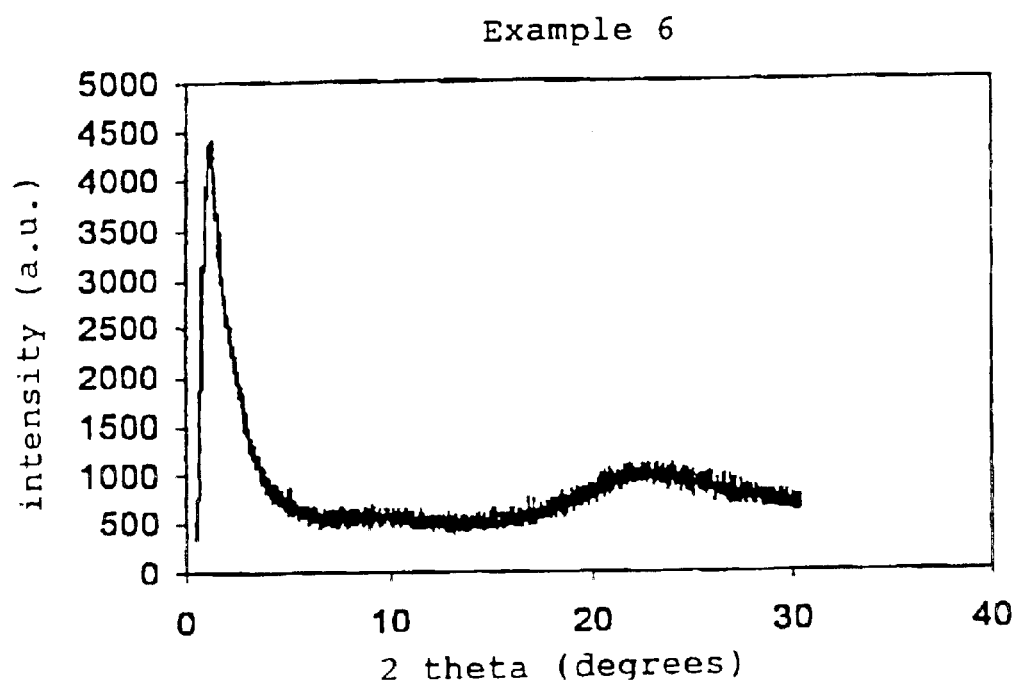
FIG. 6 is an x-ray pattern of material produced in Example 6.

FIG. 6 shows the X-ray diffraction pattern of the product. The nitrogen porosimetry data are given in Table 1.

Example 7
Synthesis of Silica with Micropores Only

A mixture of 29.12 g tetraethylene glycol (99%, ACROS) and 107.46 g water was added slowly (4–6 g/min) to 63.42 g tetraethyl orthosilicate (98%, ACROS) under stirring. The synthesis mixture was aged at room temperature for 22 h. The synthesis mixture was transferred to a dish to form a layer of approximately 1.8–2.0 cm and dried in a static air furnace at 100° C. for 24 h. The dried sample was Soxhlet extracted using chloroform for 2 days and dried in air at 100° C. The product did not have a peak in the X-ray diffraction pattern between 2Θ=0.5 and 50°. The $N_2$ porosimetry results are given in Table 1.

tribution with a peak at about 0.64 nm, corresponding to micropore size in beta zeolite. The micropore volume of pores with a diameter smaller than 0.7 nm was 0.04 $cm^3$. This is about 15.5% of the micropore volume of the pure beta zeolite. This percentage is similar to the added amount of 20 wt %, the calculated percentage of beta

TABLE 1

Nitrogen Porosimetry Data For Products of Example 1–7

| Example no. | BET ($m^2$/g) | Vmicro <10 Å ($cm^3$/g) | Vmicro 10–20 Å ($cm^3$/g) | Vmeso ($cm^3$/g) | Mesopore peak max. (nm) | Peak width at half height of mesopore peak (nm) | Percent micropores | Mesopore Ratio of half-height width to pore size at maximum height |
|---|---|---|---|---|---|---|---|---|
| 1 | 905 | 0.015 | 0.157 | 0.61 | 3.3 | .6 | 28 | 0.18 |
| 2 | 571 | 0.011 | 0.023 | 1.01 | 7.0 | .6 | 3.4 | 0.09 |
| 3 | 589 | 0.057 | 0.027 | 1.62 | 13.0 | 3.0 | 5.2 | 0.23 |
| 4 | 505 | 0.001 | 0.013 | 1.24 | | | 1.1 | 0.22 |
| 5 | 972 | 0.05 | 0.138 | 0.798 | 3.1 | 2.0 | 23 | 0.65 |
| 6 | 491 | 0.002 | 0.019 | 1.47 | 18.0 | 4.5 | 1.4 | 0.25 |
| 7 | 791 | 0.053 | 0.364 | 0.122 | n.o.*. | n.o.* | 75 | |

*n.o.: no distinct mesopore peak observed

Example 8
Synthesis of Mesoporous Material with Zeolite Beta Crystals

First, 1.48 g calcined beta zeolite with the Si/Al ratio of 4.9 and an average particle size of 1 μm was suspended into 16.32 g water and stirred for 30 minutes. Then 20.32 g tetraethylorthosilicate (TEOS) (98%, ACROS) was added into the suspension under stirring. After continuous stirring for another half hour, 9.33 g triethanolamine (98%, ACROS) was added. After stirring for another 30 minutes, 4.02 g tetraethylammonium hydroxide aqueous solution (35%, Aldrich) was added drop-wise to the mixture to increase the pH. After stirring for about 2 hours, the mixture formed a thick gel, which did not flow anymore. This gel was aged at room temperature under static conditions for 17 hours. Next, the gel was dried in air at 100° C. for 28 h. The dried gel was transferred into a 50 ml autoclave and hydrothermally treated at 170° C. for 17.5 h. Finally it was calcined at 600° C. for 10 h in air with a ramp rate of 1° C./min.

The final product, designated as beta-TUD-1, had a total weight of 7.43 gram. The theoretical amount of zeolite beta present in the product is therefore 20wt %. The material was characterized by X-ray diffraction (XRD), Transmission Electron Microscopy (TEM), nitrogen porosimetry, argon porosimetry and $NH_3$-Temperature Programmed Desorption (TPD).

Figure 7:
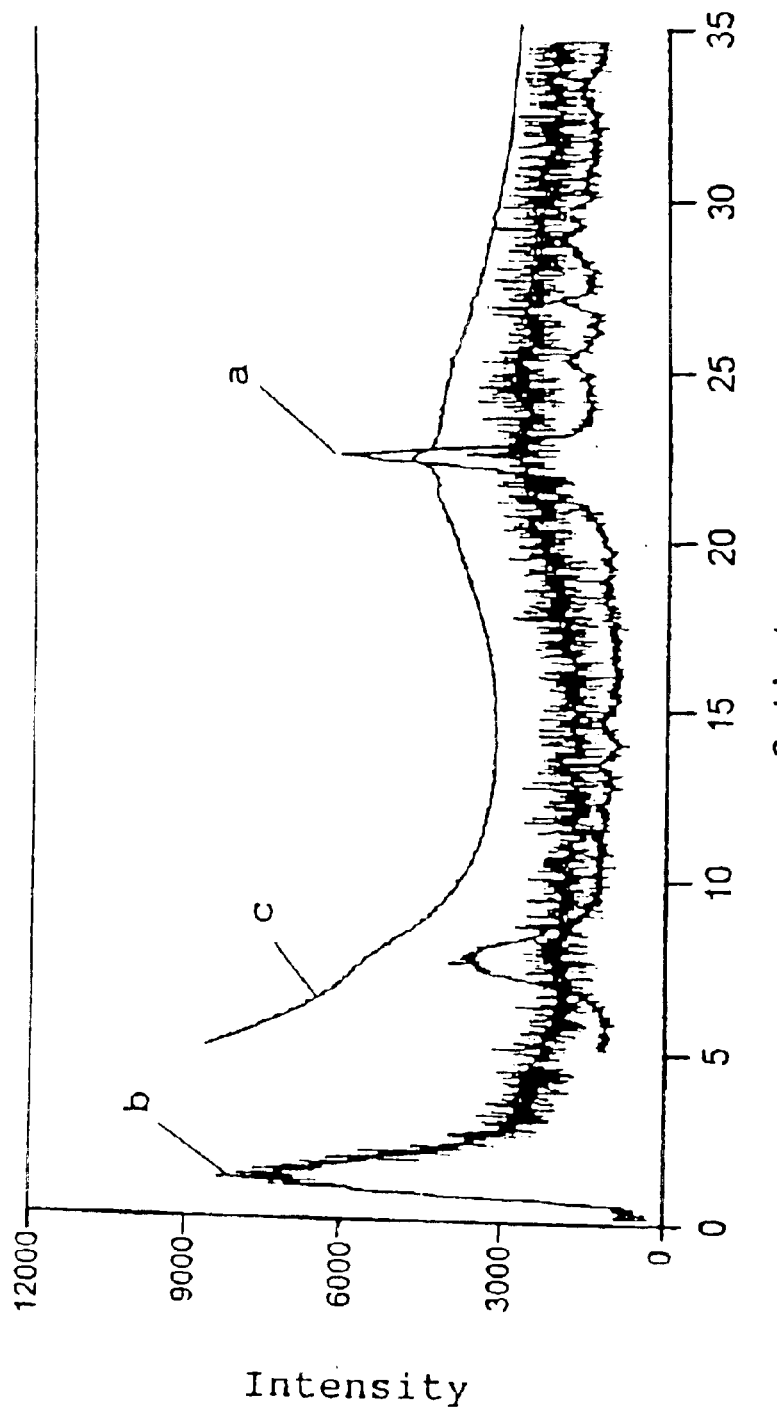
FIGS. 7a–7c are x-ray patterns of pure zeolite beta and the material produced in Example 8.

The XRD pattern of the pure beta zeolite, FIG. 7a, shows the most pronounced characteristic reflections at about 7.7° and 22.2° in 2Θ. The XRD pattern of the mesoporous with the zeolite beta crystals is shown in FIG. 7b. An intense peak at low angle is observed, indicating that beta-TUD-1 is a meso-structured material. The peaks for beta zeolite are small, since the (maximum) zeolite content of the final product is only about 20 wt %. When the scanning time was elongated from 33 minutes to 45 h, the characteristic peaks of beta zeolite become clearly visible, see FIG. 7c.

Figure 8:
FIG. 8 is a Transmission Electron Microscopy image of the material produced in Example 8.

FIG. 8 is a TEM image of beta-TUD-1, showing the features of zeolite beta crystals. This confirms that some beta zeolite crystals are present in the mesoporous matrix.

Figure 9:
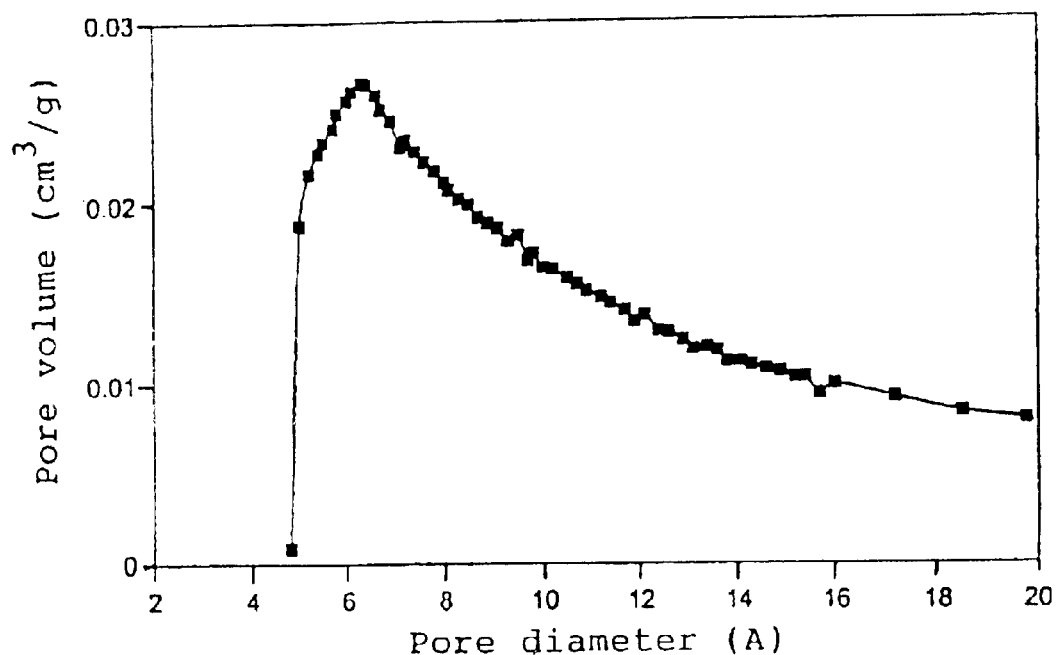
FIG. 9 is a plot of the derivative of pore volume as a function of pore diameter for the micropores of the material in Example 8.

Nitrogen adsorption shows that beta-TUD-1 has a narrow mesopore size distribution, mainly centered at about 9.0 nm, high surface area of 710 $m^2$/g and high total pore volume of 1.01 $cm^3$/g. Microporosity was measured using argon adsorption. FIG. 9 shows the micropore size diszeolite in the final product The result indicate that the zeolite can be maintained under synthesis conditions for the mesoporous silica. Furthermore, it is demonstrated that the micropore volume is accessible after the synthesis.

Figure 10:
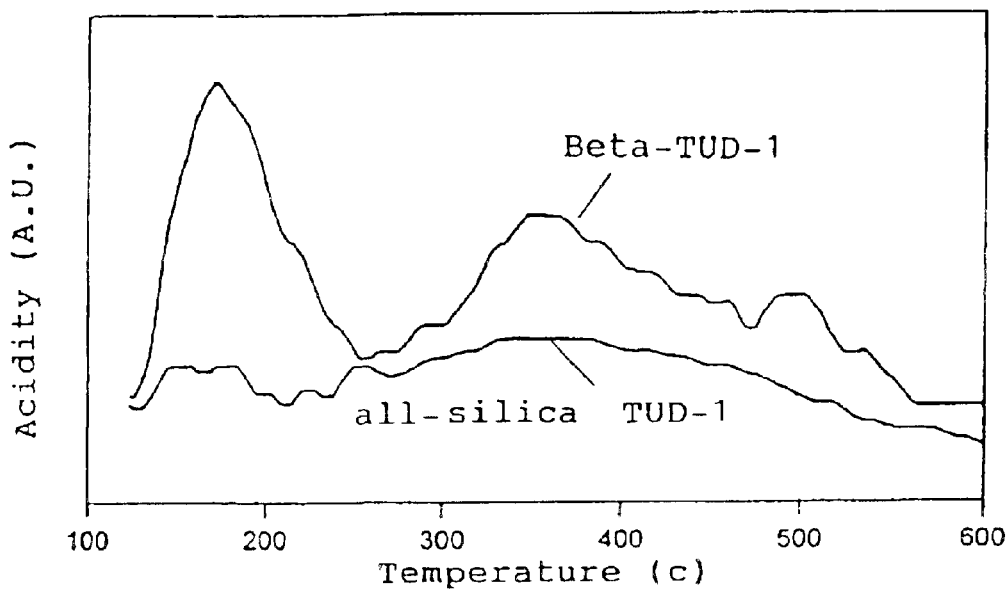
FIG. 10 is a plot of the temperature programmed desorption of ammonia from the material produced in Example 8.

$NH_3$-TPD measurement of beta-TUD-1 showed two desorption peaks, see FIG. 10, indicating that there are strong acid sites similar to those in zeolites. From comparison with the TPD-profile for the all-silica mesoporous material made according to Example 2, it is clear that the addition of beta zeolite introduces strong acid sites into mesoporous matrix.

It is understood that, although in a preferred embodiment the inorganic material is produced from silica alone or in combination with other metal oxides, it is within the spirit and scope of the invention to produce the inorganic oxide from other metals alone (for example, alumina, titania, zirconia, etc.) or combinations of metals that do not include silica.

Numerous modifications and variations of the present invention are possible in light of the above teachings and, therefore, within the scope of the appended claims, the invention may be practiced otherwise than as specifically described.

What is claimed is:

1. A process for producing an inorganic oxide that contains micro- and mesopores, comprising:
   heating a mixture comprising water, an inorganic oxide, a crystalline zeolite in finely divided form, and at least one compound that binds to the inorganic oxide by hydrogen bonding, said compound being selected from the group consisting of triethanolamine, sulfolane, tetraethylpentamine, diethylgycoldibenzoate, and a glycol, said heating being to a temperature and for a time to produce an inorganic oxide that contains both micropores and mesopores.

2. The process of claim 1 wherein said compound is triethanolamine.

3. The process of claim 1 wherein the mixture further includes a micropore forming agent.

4. The process of claim 3 wherein said micropore forming agent is a quaternary ammonium cation.

5. The process of claim 3 wherein the inorganic oxide is an amorphous silicate.

6. The process of claim 5 wherein the heating includes maintaining the mixture about the boiling point of water to evaporate water and volatile organics from the inorganic oxide, followed by calcining at a temperature of above 300° C.

7. The process of claim 1 wherein the inorganic oxide is a silicate material selected from the group consisting of tetraethyl orthosilicate, fumed silica, sodium silicate and silica sol.

8. The process of claim 1 wherein the glycol has a boiling point of at least 150° C.

9. The process of claim 8 wherein the glycol is selected from the group consisting of glycerol, diethylene glycol, triethylene glycol and tetraethylene glycol.

10. The process of claim 9 wherein the mixture additionally contains a source of ions selected from the group consisting of IVA, VB, VIB, VIIB, VIII, IB, IIB and IIIA elements.

11. The process of claim 9 wherein the mixture additionally contains a source of aluminium ions.

12. The process of claim 1 wherein the inorganic oxide comprises alumina.

13. The process of claim 1 wherein the average particle size of the zeolite is from 5 to 1500 nanometers.

14. A product comprising:
an inorganic oxide and zeolite beta, said product including mesopores and micropores, said micropores being present in an amount of from 3% to 60%, by pore volume, based on micropores and mesopores, said mesopores having been generated by an organic pore-forming agent selected from the group consisting of triethanolamine, sulfolane, tetraethylpentamine, diethylglycoldibenzoate, and a glycol.

15. The product of claim 14 wherein the BET surface area is from 50 to 1250 m$^2$/g.

16. The product of claim 14 wherein the combined micro- and mesopore volume is from 0.3 to 2.2 ml/g.

17. The product of claim 14 wherein the pore size distribution of the mesopores produces a pore size distribution plot in which the ratio of the width of the plot at half the height of the plot to the pore size at the maximum height of the plot is no greater than 0.75.

18. The product of claim 14 wherein a pore size distribution plot of mesopores and micropores includes distinct mesopore and micropore peaks.

19. The product of claim 14 wherein the inorganic oxide comprises alumina.

20. The product of claim 14 wherein the average particle size of the zeolite beta is from 5 to 1500 nanometers.

21. A process for producing an inorganic oxide that contains mesopores and a substantial amount of micropores, comprising:
heating a mixture comprising water, an inorganic oxide, a crystalline zeolite, and at least one compound that binds to the inorganic oxide by hydrogen bonding, said compound being selected from the group consisting of triethanolamine, sulfolane, tetraethylpentamine, diethylglycoldibenzoate and a glycol, said heating being to a temperature below the temperature at which there is substantial formation of mesopores, and removing said at least one compound at a temperature below the temperature at which there is substantial formation of mesopores to produce an inorganic oxide that contains mesopores and a substantial amount of micropores.

22. The process of claim 21 wherein said zeolite is zeolite beta.

23. The process of claim 21 wherein the mixture additionally contains a source of ions selected from the group consisting of IVA, VB, VIB, VIIB, VIII, IB, IIB, and IIIA elements.

24. The process of claim 21 wherein the mixture additionally contains a source of aluminum ions.

25. The process of claim 21 wherein the inorganic oxide comprises alumina.

26. The process of claim 21 wherein the average particle size of the zeolite is from 5 to 1500 nanometers.

* * * * *